(12) United States Patent
Yuan et al.

(10) Patent No.: US 10,745,334 B2
(45) Date of Patent: Aug. 18, 2020

(54) METHOD FOR SYNTHESIZING 2,3,5,6-TETRAFLUORO-4-METHOXYMETHYL BENZYL ALCOHOL

(71) Applicant: ZHEJIANG ZHONGXIN FLUORIDE MATERIALS CO., LTD., Shaoxing (CN)

(72) Inventors: Qiliang Yuan, Shaoxing (CN); Jingde Zhang, Shaoxing (CN); Haifeng Chen, Shaoxing (CN); Yixin Cui, Shaoxing (CN); Yinhao Chen, Shaoxing (CN); Chao Wang, Shaoxing (CN)

( * ) Notice: Subject to any disclaimer, the term of this patent is extended or adjusted under 35 U.S.C. 154(b) by 0 days.

(21) Appl. No.: 16/812,317

(22) Filed: Mar. 8, 2020

(65) Prior Publication Data

US 2020/0207693 A1 Jul. 2, 2020

Related U.S. Application Data

(63) Continuation of application No. PCT/CN2019/072275, filed on Jan. 18, 2019.

(51) Int. Cl.

| | | |
|---|---|---|
| *C07C 41/01* | (2006.01) | |
| *C07C 67/03* | (2006.01) | |
| *C07C 67/02* | (2006.01) | |
| *C07C 29/10* | (2006.01) | |
| *C07C 29/09* | (2006.01) | |
| *C07C 67/24* | (2006.01) | |
| *C07C 41/26* | (2006.01) | |

(52) U.S. Cl.
CPC .............. *C07C 41/26* (2013.01); *C07C 29/09* (2013.01); *C07C 29/095* (2013.01); *C07C 29/10* (2013.01); *C07C 41/01* (2013.01); *C07C 67/02* (2013.01); *C07C 67/03* (2013.01); *C07C 67/24* (2013.01)

(58) Field of Classification Search
None
See application file for complete search history.

(56) References Cited

U.S. PATENT DOCUMENTS

| | | |
|---|---|---|
| 10,392,690 B1 | 8/2019 | Alsayegh et al. |
| 2001/0003138 A1* | 6/2001 | Hirose .................... C07C 41/16 568/637 |
| 2020/0031852 A1 | 1/2020 | Murai et al. |
| 2020/0040372 A1 | 2/2020 | Tanaka et al. |

FOREIGN PATENT DOCUMENTS

| | | |
|---|---|---|
| CN | 1434021 A | 8/2003 |
| CN | 101913997 A | 12/2010 |
| CN | 107089904 A | 8/2017 |

* cited by examiner

*Primary Examiner* — Medhanit W Bahta
(74) *Attorney, Agent, or Firm* — Erson IP (Nelson IP)

(57) ABSTRACT

The disclosure discloses a method for synthesizing 2,3,5,6-tetrafluoro-4-methoxymethyl benzyl alcohol from 1,4-bis(methoxymethyl)-2,3,5,6-tetrafluorobenzene, belongings to the technical field of organic synthesis. 1,4-bis(methoxymethyl)-2,3,5,6-tetrafluorobenzene reacts in mixed solution consisting of sulfuric acid aqueous solution and organic carboxylic acid, the obtained mixture is subjected to ester group hydrolysis reaction in the presence of an inorganic base and then to hydroxyl methylation reaction, 2,3,5,6-tetrafluoro-4-methoxymethyl benzyl alcohol is finally obtained via separation and purification, and 1,4-bis(methoxymethyl)-2,3,5,6-tetrafluorobenzene is recovered. The disclosure not only realizes the resource utilization of low-value 1,4-bis(methoxymethyl)-2,3,5,6-tetrafluorobenzene, and meanwhile has the advantages of mild reaction conditions, simple operation, high synthesis yield, good product quality and the like. The disclosure has high social and economic values.

12 Claims, No Drawings

METHOD FOR SYNTHESIZING 2,3,5,6-TETRAFLUORO-4-METHOXYMETHYL BENZYL ALCOHOL

CROSS-REFERENCE TO RELATED APPLICATIONS

This application is a continuation of International Patent Application No. PCT/CN2019/072276 with a filing date of Jan. 18, 2019, designating the United States, and further claims priority to Chinese Patent Application No. 2018107278088 with a filing date of Jul. 5, 2018. The content of the aforementioned applications, including any intervening amendments thereto, are incorporated herein by reference.

TECHNICAL FIELD

The disclosure belongs to the technical field of organic synthesis, and particularly relates to a method for synthesizing 2,3,5,6-tetrafluoro-4-methoxymethyl benzyl alcohol from 1,4-bis(methoxymethyl)-2,3,5,6-tetrafluorobenzene.

BACKGROUND OF THE PRESENT INVENTION 2,3,5,6-tetrafluoro-4-methoxymethyl benzyl alcohol is a key intermediate for synthesizing tetrafluoroanisolethrin, metofluthrin and meperfluthrin. Tetrafluoroanisolethrin and metofluthrin are developed by Sumitomo Chemical Industry Co., Ltd. Meperfluthrin is developed by Jiangsu Yangnong Chemical Co., Ltd. Three of them are all low-toxicity high-efficiency pyrethroids pesticides, which have excellent knockdown and killing activity on sanitary insect pests such as mosquito and flies, and have been widely applied to controlling sanitary insect pests at present.

At present, several methods for synthesizing 2,3,5,6-tetrafluoro-4-methoxymethyl benzyl alcohol reported in documents are as follows:

(1) The document (J. Fluo. Chem. 130 (2009), 938-941) reported synthesis of 2,3,5,6-tetrafluoro-4-methoxymethylbenzyl alcohol by using 2,3,5,6-tetrafluorobenzyl alcohol as a raw material via three reaction steps of methyl etherification, carboxylation and carboxy reduction.

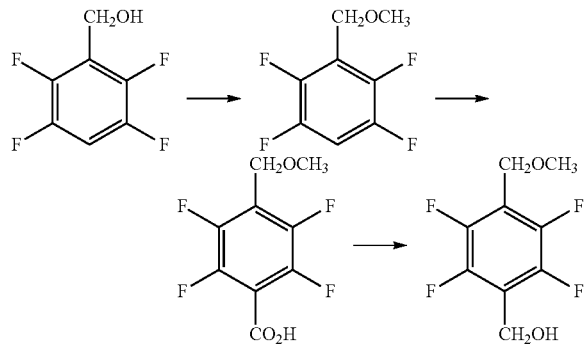

This method has a long reaction step, needs to use dangerous reagents such as strong bases and strong reducing agents in the process of synthesis, requires harsh conditions such as low temperature, and has high control requirements on reaction processes and high synthesis cost, and thus is only suitable for research rather than industrial production.

(2) Invention patent JP 2000344703 reported synthesis of 2,3,5,6-tetrafluoro-4-methoxymethylbenzyl alcohol by using tetrafluoroterephthalyl alcohol as a raw material via halogenation and methoxylation.

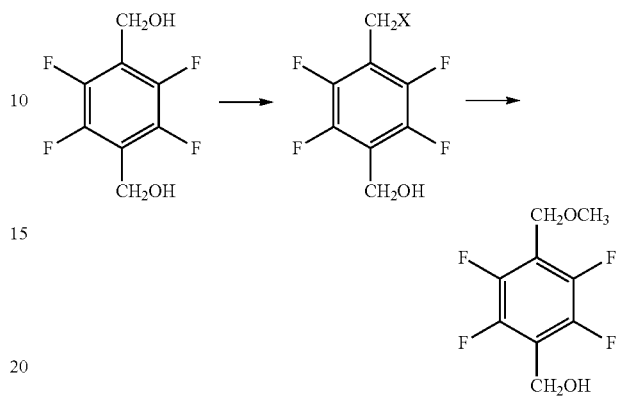

This method is short in synthesis step and obtains the product by only two steps. Furthermore, the used reagents are all industrialized conventional raw materials which are cheap and available, so this method is low in synthesis cost and suitable for industrial production. The disadvantages are that the chemical property of hydroxyl in tetrafluoroterephthalyl alcohol is similar to that of hydroxyl in the halogenation product 2,3,5,6-tetrafluoro-4-halomethylbenzyl alcohol, their selectivity is poor when halogenation reaction is carried out, dihalogenation byproducts are easily generated, and the byproduct 1,4-bis(methyoxymethyl)-2,3,5,6-tetrafluorobenzene is further generated when the subsequent methoxylation reaction is carried out, thereby, leading to reduced reaction yield and increased synthesis cost.

(3) 2,3,5,6-tetrafluoro-4-methoxymethylbenzyl alcohol is obtained by using tetrafluoro tetraphthalyl alcohol, as a raw material via selective methylation reaction in the presence of the methylation reagent.

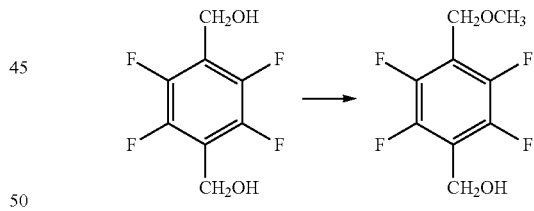

For example, invention patent CN1297875A, which is applied from Sumitomo Chemical Industry Co., Ltd. of Japan, uses dimethyl sulfate as the methylation reagent: invention patent CN101913997A, which is applied from Guizhou bositer chemical industry, uses methyl chloride as the methylation reagent. This method is short in synthesis steps, obtains the product by using only one step reaction, cheap and available in used reagent, and is a main method for industrially synthesizing 2,3,5,6-tetrafluoro-4-methoxymethylbenzyl alcohol at present. The main disadvantages are that in the process of reaction, the chemical property of hydroxyl in raw material tetrafluoroterephthalyl alcohol is similar to that of hydroxyl in the product 2,3,5,6-tetrafluoro-4-halomethylbenzyl alcohol, leading to poor selectivity in the process of reaction and easily generation, of byproduct 1,4-bis(methyoxymethyl)-2,3,5,6-tetrafluorobenzene. Typically, the content of this byproduct is about 10%, which results in reduced reaction cost and increased synthesis cost.

At present, in the industrial manufacturing process of 2,3,5,6-tetrafluoro-4-methoxymethylbenzyl alcohol, the byproduct 1,4-bis(methoxymethyl)-2,3,5,6-tetrafluorobenzene is generated. According to the different process routes and process conditions, the byproduct usually accounts for 5-15%. At present, its application value has not been found, so it can only be burned as hazardous waste, which not only pays a large amount of treatment cost but also possibly generates secondary pollution in the process of incineration disposal. Thus, how to perform resource utilization of 1,4-bis (methoxymethyl)-2,3,5,6-tetrafluorobenzene has become an urgent problem.

SUMMARY OF PRESENT INVENTION

The disclosure realizes synthesis of 2,3,5,6-tetrafluoro-4-methoxymethyl benzyl alcohol using 1,4-bis(methoxymethyl)-2,3,5,6-tetrafluorobenzene as a raw material through design of new process routes and by adopting creative process conditions, not only converts low-value 1,4-bis (methyoxymethyl)-2,3,5,6-tetrafluorobenzene into high-value 2,3,5,6-tetrafluoro-4-methoxymethyl benzyl alcohol but also allows the process to have the advantages of mild reaction conditions, cheap and available reagents, simple operation, high synthesis yield, good product quality and the like via technological innovation, and has extremely high social and economic values.

The disclosure adopts the following technical solution:

Provided is a method for synthesizing 2,3,5,6-tetrafluoro-4-methoxymethyl benzyl alcohol, comprising the following steps:

(1) reacting 1,4-bis(methoxymethyl)-2,3,5,6-tetrafluorobenzene with mixed solution consisting of sulfuric acid aqueous solution and organic carboxylic acid to obtain a mixture (II);

(2) hydrolyzing the mixture (II) in the presence of an inorganic base to obtain a mixture (III); and (3) reacting the mixture (III) with a methylation reagent in the presence of an inorganic base to obtain a mixture (IV), separating and purifying the mixture (IV) to obtain 2,3,5,6-tetrafluoro-4-methoxymethyl benzyl alcohol (V), and recovering 1,4-bis(methoxymethyl)-2,3,5,6-tetrafluorobenzene (I).

Specifically, first, the raw material 1,4-bis (methoxymethyl)-2,3,5,6-tetrafluorobenzene (I) is subjected to ether bond breaking and hydroxyl in-situ esterification reaction in a mixed solution consisting of sulfuric acid aqueous solution and organic carboxylic acid to obtain the mixture (II) consisting of a small amount of 1,4-bis (methoxymethyl)-2,3,5,6-tetrafluorobenzene (I) and a large proportion of carboxylates and alcohols; then, in the presence of the inorganic base, the carboxylate in the mixture (II) reacts with ester group hydrolysis reaction to recover the hydroxyl to obtain the mixture (III) mainly consisting of monohydric alcohol, diol and a small amount of 1,4-bis (methoxymethyl)-2,3,5,6-tetrafluorobenzene (I); subsequently, the mixture (III) undergoes the methylation reaction of hydroxyl in the presence of the inorganic base to convert the diol into monohydric alcohol to obtain the mixture (IV) mainly consisting of monohydric alcohol and a small amount of 1,4-bis(methoxymethyl) 2,3,5,6-tetrafluorobenzene (I), wherein the monohydric alcohol is 2,3,5,6-tetrafluoro-4-methoxymethylbenzyl alcohol (V); finally, the mixture (IV) is separated and purified to respectively obtain the product 2,3,5,6-tetrafluoro-4-methoxymethylbenzyl alcohol (V) and the recovered raw material 1,4-bis (methoxymethyl)-2,3,5,6-tetrafluorobenzene (I). In this solution, the low-value 1,4-bis (methoxymethyl)-2,3,5,6-tetrafluorobenzene is successfully converted into high-value 2,3,5,6-tetrafluoro-4-methoxymethylbenzyl alcohol (V) through simple and controllable reaction processes and low-cost reaction reagents. At the same time, the recovered 1,4-bis (methoxymethyl)-2,3,5,6-tetrafluorobenzene (I) can also be recycled with significant social and economic values.

The technical route adopted by the disclosure can be represented by the following reaction formula:

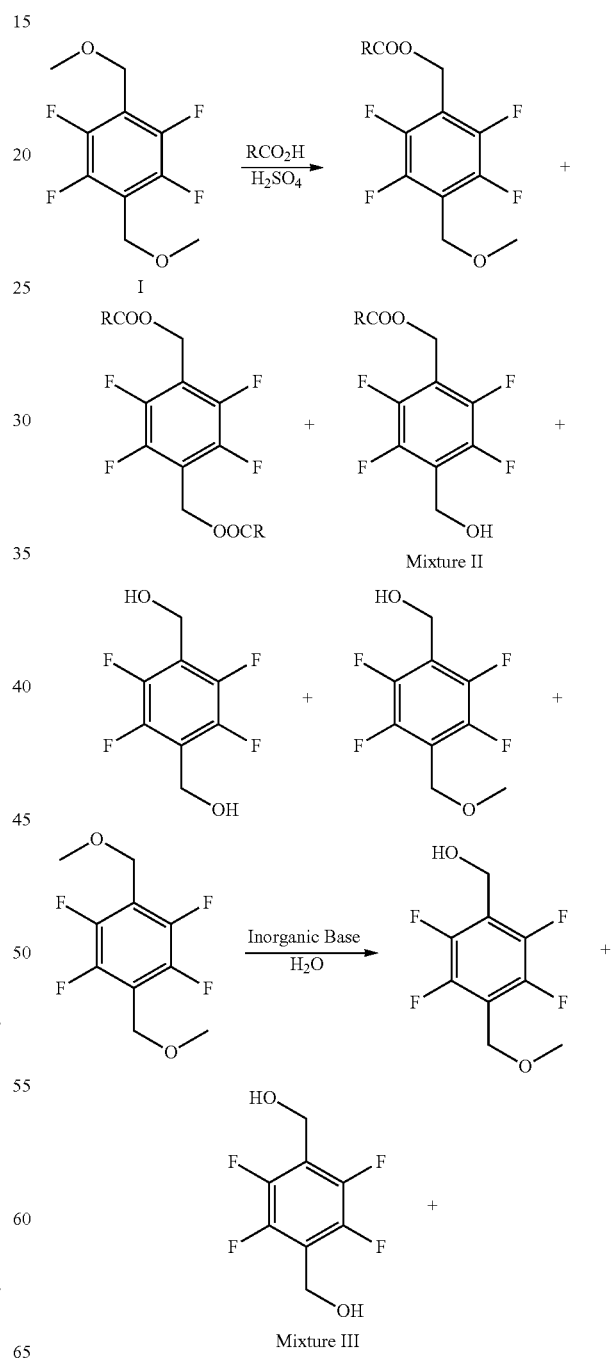

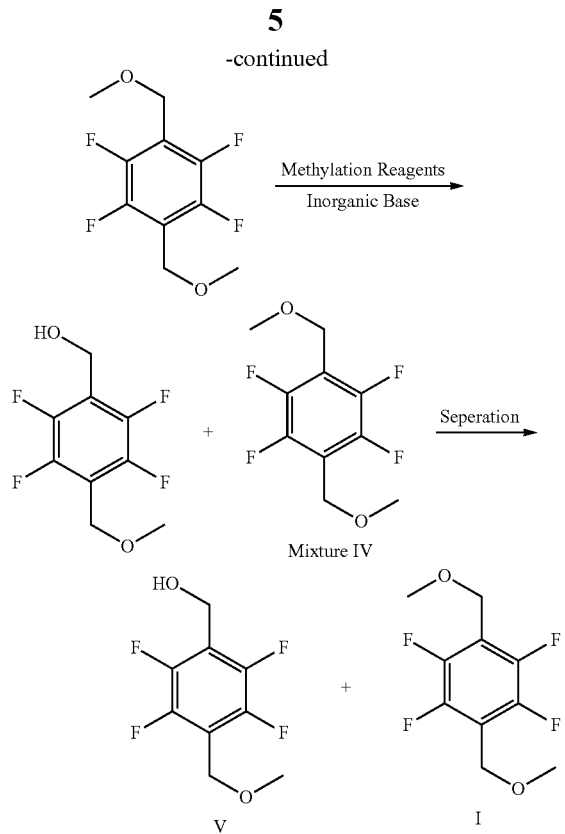

The disclosure is further set as follows:

in step (1):

research on preparation of mixed solution consisting of sulfuric acid aqueous solution and organic carboxylic acid is conducted to determine a preferred compound solution: the sulfuric acid aqueous solution is prepared from sulfuric acid and water, wherein the mass fraction of sulfuric acid is 50~90%, and the amount of sulfuric acid aqueous solution is 1~10 times the mass of the compound (I); the organic carboxylic acid refers to any one of C1~C6 linear or branched alkyl monocarboxylic acids or a combination thereof, specifically, for example, formic acid, acetic acid, propionic acid, n-butyric acid, iso-butyric acid, n-pentanoic acid, iso-pentanoic acid and hexanoic acid, preferred organic carboxylic acid is one or two of acetic acid and propionic acid. The organic carboxylic acid serves as not only a reaction solvent but also a reaction reagent, and its amount is 0.5~10 times the mass of the compound (I).

The reaction temperature is related to the concentration and amount of sulfuric acid aqueous solution as well as types and amounts of organic carboxylic acids. The reaction activity of the compound (I) varies with reaction systems consisting of the concentration and amount of different sulfuric acid aqueous solution as well as types and amounts of different organic carboxylic acids. Therefore, the reaction temperature needs to be properly regulated according to particular conditions, and the preferred reaction temperature is 90~160° C.

In the process of reaction, first, the raw material 1,4-bis (methoxymethyl)-2,3,5,6-tetrafluorobenzene (I) is subjected to ether bond breaking I the process of sulfuric acid to generate 2,3,5,6-tetrafluoro-4-methoxymethylbenzyl alcohol (V) and 2,3,5,6-tetrafluoroterephthalyl alcohol, the above ether bond breaking products are subjected to in-situ esterification reaction with organic carboxylic acid under the catalysis of sulfuric acid to generate the mixture (II) so as to realize the synchronization of ether bond breaking-hydroxyl protection of the raw material, thereby thoroughly avoiding the ether bond breaking products to perform esterification side, reaction between two molecules or multiple molecules. The mixture (II) obtained by reaction mainly consists of 2,3,5,6-tetrafluoro-4-methoxymethylbenzyl alcohol carboxylate, 2,3,5,6-tetrafluoroterephthalyl alcohol dicarboxylate, 2,3,5,6-tetrafluoroterephthalyl alcohol monocarboxylate. 2,3,5,6-tetrafluoroterephthalyl alcohol, 2,3,5,6-tetrafluoro-4-methoxymethyl benzyl alcohol (V) and 1,4-bis (methoxymethyl)-2,3,5,6-tetrafluorobenzene (I), the composition proportions of various compounds vary with change in reaction conditions and different reaction times. In the process of reaction, the content of 1,4-bis (methoxymethyl)-2,3,5,6-tetrafluorobenzene (I) and generation amounts of other impurities are used as main control parameters, for 2,3,5,6-tetrafluoro-4-methoxymethylbenzyl alcohol carboxylate, 2,3,5,6-tetrafluoroterephthalyl alcohol dicarboxylate, 2,3,5,6-tetrafluoroterephthalyl alcohol monocarboxylate and 2,3,5,6-tetrafluoroterephthalyl alcohol, they are all converted into the product (V) in the subsequent reaction process, while 2,3,5,6-tetrafluoro-4-methoxymethyl benzyl alcohol (V) itself is the product (V), thus their mutual composition proportions do not affect the reaction effect. In general, when the content of 1,4-bis (methoxymethyl)-2,3, 5,6-tetrafluorobenzene (I) in the reaction system is reduced to less than 15%, preferably less than 10%, the reaction is stopped.

After the reaction is ended, the resulting mixture (II) is mixed with sulfuric acid aqueous solution and organic carboxylic acid, the mixture (II) is separated from the reaction system through separation operation and then subjected to subsequent reaction. Therefore, a separation step is preferably set between steps (1) and (2), the preferred separation method is extraction, and the extraction solvent is selected from any one of dichloromethane, 1,2-dichloroethane, chloroform, toluene, xylene, chlorobenzene and dichlorobenzene, or a combination thereof. The selection of extraction solvent amount, extraction temperature, extraction times and the like can be properly regulated according to actual needs. The solution obtained by extraction and containing the mixture (II) can be directly used for step (2), or the mixture (II) can be obtained after the solvent is removed by distillation and then used for step (2).

In step (2):

The mixture (II) can be the mixture (II) solution obtained in step (1) and containing the extraction solvent, or the solvent-free mixture (II) obtained by removing the extraction solvent via distillation. If the mixture (II) solution containing the extraction solvent is used, the actual quantity of the mixture (II) in the solution needs to be amortized prior to use, so as to calculate the amounts of other materials.

The reaction is alkali hydrolysis reaction of organic carboxylate, in which water is used as the reaction solvent, or the mixed solvent consisting of a proper organic solvent and water as the reaction solvent. When water is used as the reaction solvent, the amount of water is 1~10 times the weight of the mixture (II). When the mixed solvent consisting of the organic solvent and water is used as the reaction solvent, the organic solvent is selected from any one of dichloromethane, 1,2-dichloroethane, chloroform, toluene, xylene, chlorobenzene and dichlorobenzene or a combination thereof, the amount of water in the mixed solvent is 1~10 times the weight of the mixture (II), and the amount of the organic solvent is no more than 10 times the mass of water. When the mixture (II) solution obtained in step (1)

and containing the extraction solvent is used, the carried extraction solvent can be used as the organic solvent, and can also be calculated within the amount of the organic solvent in step (2).

The inorganic base is selected from any one of lithium hydroxide, sodium hydroxide, potassium hydroxide, lithium carbonate, sodium carbonate, potassium carbonate, lithium bicarbonate, sodium bicarbonate, potassium bicarbonate, lithium phosphate, sodium phosphate, potassium phosphate, or a combination thereof. In the process of reaction, 2,3,5,6-tetrafluoro-4-methoxymethyl benzyl alcohol carboxylate, 2,3,5,6-tetrafluoroterephthalyl alcohol dicarboxylate, 2,3,5,6-tetrafluoroterephthalyl alcohol monocarboxylate in the mixture (II) are subjected to ester group hydrolysis reaction in the presence of the inorganic base to generate the mixture (III). The amount of the inorganic base is related to composition proportions of various compounds in the mixture (II), more clearly, to the total mole of ester groups in the mixture (II). Since there is a certain change interval in composition proportions of various compounds in the mixture (II), the total mole of ester groups in the mixture (II) is calculated according to the actual proportions of various compounds in the mixture (II) and in combination with addition quantity of the mixture (II) prior to reaction, and based on this, the amount of the inorganic base is determined to ensure complete hydrolysis of 2,3,5,6-tetrafluoro-4-methoxymethyl benzyl alcohol carboxylate, 2,3,5,6-tetrafluoroterephthalyl alcohol dicarboxylate, 2,3,5,6-tetrafluoroterephthalyl alcohol monocarboxylate in the mixture (II). The total molar ratio of the preferred inorganic base to ester groups contained in various compounds in the mixture (II) is (1~10):1.

The reaction temperature is related to types and amount of the used inorganic base and the amount of the solvent, and can be regulated within a certain range according to practical situations. A preferred reaction temperature is 30~100° C.

After the reaction is ended, the obtained mixture (III) mainly consists of 2,3,5,6-tetrafluoroterephthalyl alcohol, 2,35,6-tetrafluoro-4-methoxymethyl benzyl alcohol (V) and 1,4-bis(methoxymethyl)-2,3,5,6-tetrafluorobenzene (I). The mixture (III) can be separated from the reaction system using a proper method and then subjected to reaction of step (3), the selected separation methods include crystallization-filtration and extraction-concentration. From the viewpoints of cost, environmental protection and the like, a preferred method is that the mixed solution after the reaction is directly subjected to reaction of step (3) without any separation steps.

In step (3):

The mixture (III) can be the mixture (III) obtained via crystallization-filtration, extraction-concentration and the other operations after the reaction of the step (2) is ended, or step (2) and step (3) are directly connected in series for reaction, the mixture (III) is reaction liquid containing the mixture (III) when the reaction in step (2) is ended. Considering that ester hydrolysis of step (2) has no significant side reactions, it can be regarded as quantitative hydrolysis. Thus, the addition amount of the mixture (III) and composition proportions of various components can be calculated according to the addition amount of the mixture (II) in step (2) and composition proportions of various components, and based on this, the amounts of other materials in step (3) are determined.

The reaction is etherification reaction of alcoholic hydroxyl in the presence of the inorganic base. In the process of reaction, 2,3,5,6-tetrafluoroterephthalyl alcohol in the system is subjected to etherification reaction with a methylation reagent to generate the product (V). Meanwhile, etherification reaction of the product (V) is avoided to the greatest extent, so as to generate the byproduct 1,4-bis(methoxymethyl)-2,3-5,6-tetraflorobenzne (I).

The inorganic base is selected from any one of lithium hydroxide, sodium hydroxide, potassium hydroxide, lithium carbonate, sodium carbonate, potassium carbonate, lithium bicarbonate, sodium bicarbonate, potassium bicarbonate, lithium phosphate, sodium phosphate, potassium phosphate or a combination thereof, and the molar ratio of the inorganic base to 2,3,5,6-tetrafluoroterephthalyl alcohol contained in the mixture (III) is (1~10):1. It should be noted that if step (2) and step (3) are connected in series for reaction, excessive base in step (2) can also be used as the base in step (3), and calculated within the amount range of the base in step (3).

The methylation reagent is selected from any one of methyl chloride, methyl bromide, methyl iodide and dimethyl sulfate or a combination thereof, and the molar ratio of the methylation reagent to 2,3,5,6-tetrafluoroterephthalyl alcohol in the mixture (III) is (1~5):1.

The reaction can, be carried out in a water phase or in the mixed solvent consisting of water and the organic solvent. The preferred reaction solvent is a mixed solvent consisting of water and the organic solvent, which is beneficial to inhibiting further etherification of the product (V) and reducing the generation of the byproduct 1,4-bis(methoxymethyl)-2,3,5,6-tetrafluorobenzene (I). When water is used as the reaction solvent, the amount of water is 1~15 times the mass of the mixture (III). When the mixed solvent consisting of water and the organic solvent serves as the reaction solvent, the organic solvent is selected from any one of dichloromethane, 1,2-dichloroethane, chloroform, toluene, xylene, chlorobenzene, dichlorobenzene, cyclohexane, methyl cyclohexane, n-hexane, n-heptane, isopropyl ether and methyl tert-butyl ether or a combination thereof, the mass ratio of water to organic solvent is (0.1~10):1, and the amount of the mixed solvent is 1~15 times the weight of the mixture (III). If the mixture (II) used in step (2) is the mixture (II) solution obtained in step (1) and containing the extraction solvent and step (2) and step (3) are connected in series for reaction, the extraction solvent in step (1) can also be used as the organic solvent in step (3) and calculated within the amount range of the organic solvent in step (3). Meanwhile, the amount of water in step (2) can also be used as the amount of water in step (3) and calculated within the amount range of the water used in step (3).

The reaction temperature is related to types of the used methylation reagent and types and amount of inorganic base as well as composition and amount of the solvent and can be regulated within a certain range according to practical situations, and a preferred reaction temperature is 20~80° C.

After the reaction is ended, the mixture (IV) mainly consisting of the product 4-methoxymethyl-2,3,5,6-tetrafluorobenzyl alcohol (V) and the byproduct 1,4-bis(methoxymethyl)-2,3,5,6-tetrafluorobenzene (I) is obtained, and the product 4-methoxymethyl-2,3,5,6-tetrafluorobenzyl alcohol (V) and the byproduct 1,4-bis(methoxymethyl)-2,3,5,6-tetrafluorobenzene (I) are obtained by separation and purification. The selected separation methods include rectification and recrystallization, the byproduct 1,4-bis(methoxymethyl)-2,3,5,6-tetrafluorobenzene (I) obtained by separation and recovery is used as a raw material to synthesize 4-methoxymethyl-2,3,5,6-tetrafluorobenzyl alcohol (V) again.

Compared with the prior art, this application has the beneficial effects:

(1) 2,3,5,6-tetrafluoro-4-methoxymethyl benzyl alcohol is synthesized by using the byproduct 1,4-bis (methoxymethyl)-2,3,5,6-tetrafluorobenzene as the raw material generated in the process of industrially manufacturing 2,3,5,6-tetrafluoro-4-methoxymethylbenzyl alcohol, thereby realizing the resource and recycling of the byproduct.

(2) The mixed solution consisting of sulfuric acid aqueous solution and organic carboxylic acid is used to perform ether bond breaking reaction, which avoids esterification side reaction between two molecules or multiple molecules when sulfuric acid aqueous solution is only used for ether bond breaking, and hydroxyl in carboxylate generated by derivation can be, recovered via simple alkaline hydrolysis reaction.

(3) The reaction reagent used in this application is cheap and available and has the advantages of mild reaction conditions, simple operation, high yield, good product quality and the like, the byproduct 1,4-bis (methoxymethyl)-2,3,5,6-tetrafluorobenzene generated in the process of reaction can be recycled, and social and economic values are significant.

DETAILED DESCRIPTION OF PREFERRED EMBODIMENTS

Example 1

140 g of compound (I), 420 g of 70% sulfuric acid aqueous solution and 1120 g of propionic acid were added into a 2 L reaction bottle, stirred, heated to 140-145° C., preserved and reacted for 10 hours, the reaction was stopped and the temperature was reduced. The reaction liquid was extracted with 700 g of chloroform, organic phases were combined, and chloroform was removed by vacuum distillation, so as to obtain 159.5 g of mixture (II) (HPLC detection: 35.5% of 2,3,5,6-tetrafluoro-4-methoxymethylbenzyl alcohol propionate, 20.2% of 2,3,5,6-tetrafluoroterephthalyl alcohol dipropionate, 16.8% of 2,3,5,6-tetrafluoroterephthalyl alcohol monopropionate, 4.8% of 2,3,5,6-tetrafluoroterephthalyl alcohol, 11.8% of 2,3,5,6-tetrafluoro-4-methoxymethylbenzyl alcohol and 9.1% of 1,4-bis (methoxymethyl)-2,3,5,6-tetrafluorobenzene) for the next reaction.

The obtained mixture (II) was added into a 2 L reaction bottle, 1250 g of water and 370 g of potassium carbonate were added, stirred, heated to 90-95° C. preserved for 12 hours, the reaction was stopped and the temperature was reduced, so as to obtain the mixture (III) (HPLC detection: 47.1% of 2,3,5,6-tetrafluoro-4-methoxymethylbenzyl alcohol, 41.6% of 2,3,5,6-tetrafluoroterephthalyl alcohol and 9.1% of 1,4-bis (methoxymetrehyl)-2,3,5,6-tetrafluorobenzene) for the next step.

250 g of toluene was added into the system, the temperature was controlled to 40-45° C., and 60 g of dimethyl sulfate was slowly dropwise added. After dropwise addition, the system was preserved and reacted at 40-45° C. for 2 hours, the reaction was stopped and the temperature was reduced. The reaction liquid was layered by standing to separate out an organic phase, a water phase was extracted with 200 g of toluene, organic phases were combined, the solvent was removed by vacuum distillation, the concentrate was rectified at reduced pressure to obtain 99.8 g of product (V) which has a content of 99.2% and a yield of 75.7%. 16.1 g of compound (I) was recovered, which has a content of 98.2% and a recovery rate of 11.5%.

Example 2

150 g of compound (I), 600 g of 60% sulfuric acid aqueous solution and 900 g of acetic acid were added into a 2 L reaction bottle, stirred, heated to 120-125° C., preserved and reacted for 8 hours, the reaction was stopped and the temperature was reduced. The reaction liquid was extracted with 960 g of toluene, and organic phases were combined, so as to obtain 1125 g of toluene solution of mixture (II) (HPLC detection: 32.5% of 2,3,5,6-tetrafluoro-4-methoxymethylbenzyl alcohol acetate, 22.4% of 2,3,5,6-tetrafluoroterephthalyl alcohol diacetate, 17.8% of 2,3,5,6-tetrafluoroterephthalyl alcohol monoacetate, 5.4% of 2,3,5,6-tetrafluoroterephthalyl alcohol, 11.6% of 2,3,5,6-tetrafluoro-4-methoxymethylbenzyl alcohol and 8.2% of 1,4-bis (methoxymethyl)-2,3,5,6-tetrafluorobenzene) for the next reaction.

The toluene solution of the mixture (II) was added into a 2 L reaction bottle, 480 g of water and 84 g of potassium hydroxide were added, stirred and heated to 60-65° C., preserved and reacted for 8 h, the reaction was stopped and the temperature was reduced, so as to obtain the mixture (III) (HPLC detection: 44.1% of 2,3,5,6-tetrafluoro-4-methoxymethylbenzyl alcohol, 45.3% of 2,3,5,6-tetrafluoroterephthalyl alcohol and 8.2% of 1,4-bis (methoxymetrehyl)-2,3,5,6-tetrafluorobenzene) for the next step.

40 g of potassium hydroxide was added into the system, the temperature was controlled to 50-55° C., and 72 g of dimethyl sulfate was slowly dropwise added. After dropwise addition, the system was preserved and reacted at 50-55° C. for 2 hours, the reaction was stopped and the temperature was reduced. The reaction liquid was layered by standing to separate out an organic phase, a water phase was extracted with 200 g of toluene, organic phases were combined, the solvent was removed by vacuum distillation, and the concentrate was rectified at reduced pressure to obtain 108 g of product (V) which has a content of 99.3% and a yield of 76.5%. 16.8 g of compound (I) was recovered which has a content of 98.3% and a recovery rate of 11.2%.

Example 3

160 g of compound (I), 1280 g of 80% sulfuric acid aqueous solution and 480 g of acetic acid were added into a 2 L reaction bottle, stirred, heated to 110-115° C., preserved and reacted for 9 hours, the reaction was stopped and the temperature was reduced. The reaction liquid was extracted with 350 g of dichloroethane, and organic phases were combined, so as to obtain 525 g of dichloroethane solution of mixture (II) (HPLC detection: 33.4% of 2,3,5,6-tetrafluoro-4-methoxymethylbenzyl alcohol acetate, 22.3% of 2,3,5,6-tetrafluoroterephthalyl alcohol diacetate, 18.1% of 2,3,5,6-tetrafluoroterephthalyl alcohol monoacetate, 3.4% of 2,3,5,6-tetrafluoroterephthalyl alcohol, 14.3% of 2,3,5,6-tetrafluoro-4-methoxymethylbenzyl alcohol and 6.8% of 1,4-bis (methoxymethyl)-2,3,5,6-tetrafluorobenzene) for the next reaction.

The dichloroethane solution of the obtained mixture (II) was added into a 2 L reaction bottle, 1000 g of water and 240 g of sodium carbonate were added, stirred, heated to 50-55° C., preserved and reacted for 14 hours, the reaction was stopped and the temperature was reduced, and the mixture (III) (HPLC detection: 47.6% of 2,3,5,6-tetrafluoro-4-methoxymethylbenzyl alcohol, 43.7% of 2,3,5,6-tetrafluoroterephthalyl alcohol and 6.8% of 1,4-bis (methoxymethrehyl)-2,3,5,6-tetrafluorobenzene) was obtained for the next step.

The reaction liquid was converted into a 3 L autoclave, 60 g of potassium carbonate and 70 g of methyl bromide were added, the autoclave was sealed, stirred and heated to 60~65° C., preserved and reacted for 6 h, the reaction was stopped and the temperature was reduced. The reaction liquid was layered by standing to separate out an organic phase, a water phase was extracted with 200 g of dichloroethane, organic phases were combined, the solvent was removed by vacuum distillation, and the concentrate was rectified at reduced pressure to obtain 119.7 g of product (V) which has a content of 99.0% and a yield of 78.8%. 14.2 g of compound (I) was recovered, which has a content of 98.5% and a yield of 8.9%.

Example 4

200 g of compound (I), 1200 g of 50% sulfuric acid aqueous solution and 200 g of acetic acid were added into a 2 L reaction bottle, stirred, heated to 120-125° C., preserved and reacted for 12 hours, the reaction was stopped and the temperature was reduced. The reaction liquid was extracted with 850 g of xylene, and organic phases were combined, so as to obtain 1075 g of xylene solution of mixture (II) (HPLC detection: 36.8% of 2,3,5,6-tetrafluoro-4-methoxymethylbenzyl alcohol acetate, 25.6% of 2,3,5,6-tetrafluoroterephthalyl alcohol diacetate, 15.2% of 2,3,5,6-tetrafluoroterephthalyl alcohol monoacetate, 2.5% of 2,3,5,6-tetrafluoroterephthalyl alcohol, 8.9% of 2,3,5,6-tetrafluoro-4-methoxymethylbenzyl alcohol and 9.5% of 1,4-bis (methoxymethyl)-2,3,5,6-tetrafluorobenzene) for the next reaction.

The xylene solution of the obtained mixture (II) was added into a 3 L reaction bottle, 850 g of water and 70 g of sodium hydroxide were added, stirred, heated to 80-85° C., preserved for 9 hours, the reaction was stopped and the temperature was reduced, so as to obtain the mixture (III) (HPLC detection: 45.3% of 2,3,5,6-tetrafluoro-4-methoxymethylbenzyl alcohol, 43.1% of 2,3,5,6-tetrafluoroterephthalyl alcohol and 9.5% of 1,4-bis (methoxymethrehyl)-2,3,5,6-tetrafluorobenzene) for the next step.

15 g of sodium hydroxide was added into the system, the temperature was controlled to 30-35° C., and 70 g of dimethyl sulfate was slowly dropwise added. After dropwise addition, the system was preserved and reacted at 30-35° C. for 5 hours, the reaction was stopped and the temperature was reduced. The reaction liquid was layered by standing to separate out an organic phase, a water phase was extracted with 200 g of xylene, organic phases were combined, the solvent was removed by vacuum distillation, and the concentrate was rectified at reduced pressure to obtain 142.3 g of product (V) which has a content of 99.2% and a yield of 75.6%, 24.2 g of compound (I) was recovered, which has a content of 98.1% and a yield of 12.1%.

Example 5

180 g of compound (I), 360 g of 90% sulfuric acid aqueous solution and 900 of propionic acid were added into a 2 L reaction bottle, stirred, heated to 130-135° C., preserved and reacted for 6 hours, the reaction was stopped and the temperature was reduced. The reaction liquid was extracted with 600 g of chlorobenzene, and organic phases were combined, so as to obtain 206 g of mixture (II) (HPLC detection: 31.5% of 2,3,5,6-tetrafluoro-4-methoxymethylbenzyl alcohol acetate, 21.2% of 2,3,5,6-tetrafluoroterephthalyl alcohol diacetate, 14.5% of 2,3,5,6-tetrafluoroterephthalyl alcohol mono acetate, 6.5% of 2,3,5,6-tetrafluoroterephthalyl alcohol, 16.4% of 2,3,5,6-tetrafluoro-4-methoxymethylbenzyl alcohol and 7.6% of 1,4-bis (methoxymethyl)-2,3,5,6-tetrafluorobenzene) for the next reaction.

The obtained mixture (II) was added into a 2 L reaction bottle, 400 g of water, 1400 g of chlorobenzene and 80 g of sodium hydroxide were added, stirred, heated to 70-75° C., preserved and reacted for 6 hours, the reaction was stopped and the temperature was reduced, so as to obtain the mixture (III) (HPLC detection: 47.8% of 2,3,5,6-tetrafluoro-4-methoxymethylbenzyl alcohol, 42.1% of 2,3,5,6-tetrafluoroterephthalyl alcohol and 7.6% of 1,4-bis (methoxymethrehyl)-2,3,5,6-tetrafluorobenzene) for the next step.

The reaction liquid was converted into a 3 L autoclave, 35 g of sodium carbonate was added, the system was closed, 56 g of methyl chloride gas was introduced, stirred, heated to 70~75° C., preserved and reacted for 5 h, the reaction was stopped and the temperature was reduced. The reaction liquid was layered by standing to separate out an organic phase, a water phase was extracted with 200 g of chlorobenzene, organic phases were combined, the solvent was removed by vacuum distillation, and the concentrate was rectified at reduced pressure to obtain 131.6 g of product (V) which has a content of 99.0% and a yield of 77.7%. 16.6 g of compound (I) was recovered, which has a content of 98.2% and a yield of 9.2%.

Comparative Example 40 g of compound (I) and 160 g of 60% sulfuric acid solution were added into a 250 ml reaction bottle, stirred, heated to 120-125° C. for 12 hours, the reaction was stopped and the temperature was reduced. The reaction liquid was subjected to HPLC detection: 14.5% of 2,3,5,6-tetrafluoro-4-methoxymethylbenzyl alcohol, 22.1% of 2,3,5,6-tetrafluoroterephthalyl alcohol and 21.8% of 1,4-bis (methoxymethrehyl)-2,3,5,6-tetrafluorobenzene, 23.3% of dimolecular etherified impurity, 10.4% of trimolecular etherified impurity and 7.9% of other unknown impurities.

We claim:

1. A method for synthesizing 2,3,5,6-tetrafluoro-4-methoxymethyl benzyl alcohol from 1,4-bis(methoxymethyl)-2,3,5,6-tetrafluorobenzene, comprising the following steps:
   (1) reacting 1,4-bis(methoxymethyl)-2,3,5,6-tetrafluorobenzene (I) with mixed solution consisting of sulfuric acid aqueous solution and organic carboxylic acid to obtain a mixture (II);
   (2) hydrolyzing the mixture (II) in the presence of an inorganic base to obtain a mixture (III); and
   (3) reacting the mixture (III) with a methylation reagent in the presence of an inorganic base to obtain a mixture (IV), separating and purifying the mixture (IV) to obtain 2,3,5,6-tetrafluoro-4-methoxymethyl benzyl alcohol (V), and recovering 1,4-bis(methoxymethyl)-2,3,5,6-tetrafluorobenzene (I).

2. The method for synthesizing 2,3,5,6-tetrafluoro-4-methoxymethyl benzyl alcohol according to claim 1, wherein in step (1), the sulfuric acid aqueous solution is prepared from sulfuric acid and water; the mass fraction of sulfuric acid is 50-90%, and the amount of sulfuric acid aqueous solution is 1-10 times the mass of 1,4-bis(methoxymethyl)-2,3,5,6-tetrafluorobenzene.

3. The method for synthesizing 2,3,5,6-tetrafluoro-4-methoxymethyl benzyl alcohol according to claim 1, wherein in step (1), the organic carboxylic acid at least one or a combination selected the group consisting of C1-C6 linear, branched alkyl monocarboxylic acids, or a combination thereof; and the amount of organic carboxylic acid is 0.5-10 times the mass of 1,4-bis(methoxymethyl)-2,3,5,6-tetrafluorobenzene.

4. The method for synthesizing 2,3,5,6-tetrafluoro-4-methoxymethyl benzyl alcohol according to claim 1, wherein in step (1), the organic carboxylic acid at least one or a combination selected the group consisting of formic acid, acetic acid, propionic acid, n-butyric acid, isobutyric acid, n-pentanoic acid, isopentanoic acid, and hexanoic acid.

5. The method for synthesizing 2,3,5,6-tetrafluoro-4-methoxymethyl benzyl alcohol according to claim 1, wherein the reaction temperature of step (1) is 90-160° C.

6. The method for synthesizing 2,3,5,6-tetrafluoro-4-methoxymethyl benzyl alcohol according to claim 1, wherein in step (2), the reaction solvent is water or a mixed solvent consisting of water and an organic solvent; wherein when water serves as the reaction solvent, the amount of water is 1-10 times the weight of the mixture (II); wherein when the mixed solvent consisting of water and the organic solvent serves as the reaction solvent, the organic solvent at least one or a combination selected the group consisting of dichloromethane, 1,2-dichloroethane, chloroform, toluene, xylene, chlorobenzene, and dichlorobenzene; the amount of water in the mixed solvent is 1-10 times the weight of the mixture (II), and the amount of the organic solvent is no more than 10 times the mass of water.

7. The method for synthesizing 2,3,5,6-tetrafluoro-4-methoxymethyl benzyl alcohol according to claim 1, wherein in step (2), the inorganic base at least one or a combination selected the group consisting of lithium hydroxide, sodium hydroxide, potassium hydroxide, lithium carbonate, sodium carbonate, potassium carbonate, lithium bicarbonate, sodium bicarbonate, potassium bicarbonate, lithium phosphate, sodium phosphate, and potassium phosphate; and the total molar ratio of the inorganic base to ester groups contained in the mixture (II) is (1-10):1.

8. The method for synthesizing 2,3,5,6-tetrafluoro-4-methoxymethyl benzyl alcohol according to claim 1, wherein the reaction temperature of step (2) is 30-100° C.

9. The method for synthesizing 2,3,5,6-tetrafluoro-4-methoxymethyl benzyl alcohol according to claim 1, wherein in step (3), the inorganic base at least one or a combination selected the group consisting of lithium hydroxide, sodium hydroxide, potassium hydroxide, lithium carbonate, sodium carbonate, potassium carbonate, lithium bicarbonate, sodium bicarbonate, potassium bicarbonate, lithium phosphate, sodium phosphate, and potassium phosphate; and the molar ratio of the inorganic base to 2,3,5,6-tetrafluoroterephthalyl alcohol contained in the mixture (III) is (1-10):1.

10. The method for synthesizing 2,3,5,6-tetrafluoro-4-methoxymethyl benzyl alcohol according to claim 1, wherein in step (3), the methylation reagent at least one or a combination selected the group consisting of methyl chloride, methyl bromide, methyl iodide, and dimethyl sulfate; and the molar ratio of the methylation reagent to 2,3,5,6-tetrafluoroterephthalyl alcohol in the mixture (III) is (1-5):1.

11. The method for synthesizing 2,3,5,6-tetrafluoro-4-methoxymethyl benzyl alcohol according to claim 1, wherein in step (3), the reaction solvent is water or a mixed solvent consisting of water and an organic solvent; wherein when water serves as the reaction solvent, the amount of water is 1-15 times the weight of the mixture (III); wherein when the mixed solvent consisting of water and the organic solvent serves as the reaction solvent, the organic solvent at least one or a combination selected the group consisting of dichloromethane, 1,2-dichloroethane, chloroform, methylbenzene toluene, xylene, chlorobenzene, dichlorobenzene, cyclohexane, methyl cyclohexane, n-hexane, n-heptane, isopropyl ether, and methyl tert-butyl ether; the mass ratio of water to the organic solvent is (0.1-10):1, and the amount of the mixed solvent is 1-15 times the weight of the mixture (III).

12. The method for synthesizing 2,3,5,6-tetrafluoro-4-methoxymethyl benzyl alcohol according to claim 1, wherein the reaction temperature of step (3) is 20-80° C.

* * * * *